US012268557B2

(12) United States Patent
Kolen et al.

(10) Patent No.: US 12,268,557 B2
(45) Date of Patent: *Apr. 8, 2025

(54) ULTRASOUND IMAGE PROCESSING

(71) Applicant: KONINKLIJKE PHILIPS N.V., Eindhoven (NL)

(72) Inventors: Alexander Franciscus Kolen, Eindhoven (NL); Harm Jan Willem Belt, Weert (NL); Godefridus Antonius Harks, Rijen (NL); Geert Gerardus Henricus Maria Gijsbers, Liempde (NL); Hong Liu, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/219,214

(22) Filed: Jul. 7, 2023

(65) Prior Publication Data

US 2023/0355213 A1 Nov. 9, 2023

Related U.S. Application Data

(63) Continuation of application No. 16/646,714, filed as application No. PCT/EP2018/074344 on Sep. 10, 2018, now Pat. No. 11,730,453.

(30) Foreign Application Priority Data

Sep. 14, 2017 (EP) .................................... 17191022

(51) Int. Cl.
*A61B 8/08* (2006.01)
*A61B 8/00* (2006.01)
*A61B 8/12* (2006.01)

(52) U.S. Cl.
CPC .......... *A61B 8/5246* (2013.01); *A61B 8/0841* (2013.01); *A61B 8/0883* (2013.01);
(Continued)

(58) Field of Classification Search
CPC ... A61B 8/5246; A61B 8/0841; A61B 8/0883; A61B 8/12; A61B 8/4245; A61B 8/461; A61B 8/5284; A61B 8/543; A61B 8/5269
See application file for complete search history.

(56) References Cited

U.S. PATENT DOCUMENTS 6,515,657 B1  2/2003  Zanelli
8,795,178 B2  8/2014  Hansegard et al.
(Continued)

OTHER PUBLICATIONS

International Search Report and Written Opinion for International Application No. PCT/EP2018/074344, filed Sep. 10, 2018, 12 pages.

*Primary Examiner* — Sean D Mattson (57) ABSTRACT

An ultrasound image processing apparatus includes an image processor arrangement that receives a plurality of ultrasound images. Each ultrasound image shows an invasive medical device relative to an anatomical feature during a cardiac cycle. At different phases of the cardiac cycle, the anatomical feature has a different shape. The ultrasound processing apparatus compiles groups of the ultrasound images with ultrasound images in each group belonging to the same phase of the cardiac cycle. The ultrasound image processing apparatus generates an augmented ultrasound image from one of the ultrasound images by removing a shadow region on the anatomical feature of interest caused by the invasive medical device based on a displacement of the invasive medical device.

14 Claims, 6 Drawing Sheets

(52) U.S. Cl.
CPC .............. *A61B 8/12* (2013.01); *A61B 8/4245* (2013.01); *A61B 8/461* (2013.01); *A61B 8/5284* (2013.01); *A61B 8/543* (2013.01)

(56) References Cited

U.S. PATENT DOCUMENTS

| | | | |
|---|---|---|---|
| 9,301,733 B2 | 4/2016 | Gerard et al. | |
| 11,730,453 B2* | 8/2023 | Kolen | A61B 8/461 600/440 |
| 2007/0167801 A1* | 7/2007 | Webler | G06T 19/00 600/459 |
| 2008/0146942 A1 | 6/2008 | Dala-Krishna | |
| 2014/0100439 A1* | 4/2014 | Jones | G06T 7/0016 600/407 |
| 2014/0270436 A1 | 9/2014 | Dascal et al. | |
| 2016/0089116 A1 | 3/2016 | Duncan et al. | |

\* cited by examiner

ULTRASOUND IMAGE PROCESSING

RELATED APPLICATIONS

This application is a continuation application of U.S. patent application Ser. No. 16/646,714, filed on Mar. 12, 2020, which in turn is the U.S. National Phase application under 35 U.S.C. § 371 of International Application No. PCT/EP2018/074344, filed on Sep. 10, 2018, which claims priority to and the benefit of European Application No. 17191022.7, filed Sep. 14, 2017. These applications are hereby incorporated by reference herein.

FIELD OF THE INVENTION

The present invention relates to an ultrasound image processing apparatus comprising an image processor arrangement adapted to receive and process a plurality of ultrasound images.

The present invention further relates to an ultrasound imaging system comprising such an ultrasound image processing apparatus.

The present invention still further relates to a method of processing a plurality of ultrasound images with such an ultrasound image processing apparatus.

The present invention still further relates to a computer program product for implementing such a method on such an ultrasound image processing apparatus.

BACKGROUND OF THE INVENTION

Ultrasound imaging is rapidly gaining popularity as an imaging technique supporting interventional procedures, either as a standalone technique or in combination with other imaging techniques such as x-ray imaging techniques. During such interventional procedures, an invasive medical device such as a catheter, guide wire, needle, and so on, is inserted into a patient by a medical professional, with the imaging tools such as ultrasound imaging being used to guide the invasive medical device towards or past anatomical regions of interest within the patient. In particular, 3-D or volumetric ultrasound imaging is a powerful tool to assist the medical professional in guiding the invasive medical device through the patient's anatomy.

A common problem during such interventional procedures is that part of an anatomical feature of interest of the patient may be blocked from view by the invasive medical device. This typically occurs in a situation where the invasive medical device is located in between the ultrasound transducer or probe and the anatomical feature of interest, in which case the invasive medical device can cast an acoustic shadow onto the anatomical feature of interest, thereby yielding an incomplete view of the anatomical feature of interest. This is of course undesirable, as it hampers the medical professional in the correct operation or guidance of the invasive medical device relative to the incompletely imaged anatomical feature of interest.

Solutions exist to address the problem of such acoustic shadowing of part of an anatomical region of interest. For example, US 2014/0100439 A1 discloses a method and system for the removal of guidewire artefacts from ultrasound images. At least two ultrasound images of an imaging surface are acquired. Each acquired ultrasound image comprises a set of data. A guidewire artefact is detected in one of the at least two images. The guidewire artefacts is replaced with data representing the imaging surface obtained from another one of the at least two images.

This technique assumes that the imaging surface is the same between the different acquired ultrasound images. This, however, often is an oversimplification that can lead to incorrect artefact removal. Many invasive medical devices are inserted into the patient's cardiovascular system, e.g. to access the patient's heart or arteries. As is well-known per se, the cardiac cycle consists of different phases, e.g. expansion and contraction phases, during which various parts of the cardiovascular system, most notably the heart, change shape. Consequently, it is not straightforward to correct shadow artefacts in ultrasound images of an anatomical feature of interest that changes shape during the cardiac cycle, as the changes in the geometry of the anatomical feature of interest can cause the introduction of artefacts in a composite ultrasound image in which parts of different ultrasound images captured during such a cardiac cycle are combined due to different parts of the anatomy being combined in such a composite ultrasound image.

SUMMARY OF THE INVENTION

The present invention seeks to provide an ultrasound image processing apparatus that is configured to remove shadow regions from such imaged anatomical regions of interest in a more robust manner.

The present invention further seeks to provide an ultrasound imaging system comprising such an ultrasound image processing apparatus.

The present invention still further seeks to provide a method for removing shadow regions from such imaged anatomical regions of interest in a more robust manner.

The present invention still further seeks to provide a computer program product for implementing such a method on an ultrasound image processing apparatus.

According to an aspect, there is provided an ultrasound image processing apparatus comprising an image processor arrangement adapted to receive a plurality of ultrasound images, each ultrasound image imaging an invasive medical device relative to an anatomical feature of interest during a particular phase of a cardiac cycle, said anatomical feature of interest having a different shape at different phases of the cardiac cycle, the plurality of ultrasound images covering at least two cardiac cycles during which the invasive medical device is displaced relative to the anatomical feature of interest; compile a plurality of groups of the ultrasound images, wherein the ultrasound images in each group belong to the same phase of said cardiac cycles; and for each group determine the displacement of the invasive medical device relative to the anatomical feature of interest between at least two ultrasound images in said group; and generate an augmented ultrasound image from one of the ultrasound images of the at least two ultrasound images by removing a shadow region on the anatomical feature of interest caused by the invasive medical device from said ultrasound image based on the determined displacement of the invasive medical device.

The present invention is based on the insight that ultrasound images, e.g. volumetric images, captured at the same phase of different cardiac cycles will capture the anatomical feature of interest, e.g. a beating heart or another part of the cardiovascular system of the patient, in substantially the same shape or geometry. Therefore, by decomposing sequences of ultrasound images of different cardiac cycles and regrouping these ultrasound images to form groups of ultrasound images wherein within each group all ultrasound images correspond to the same phase of different cardiac cycles, in each group the anatomical feature of interest has a substantially constant shape between the different ultrasound images within the group, such that any change between the ultrasound images can be attributed to the displacement of the invasive medical device relative to the anatomical feature of interest. This facilitates an accurate removal of the acoustic shadow region on the anatomical feature of interest by the invasive medical device blocking the ultrasound waves from the ultrasound probe generating such ultrasound images, as the risk of introducing artefacts in such an augmented ultrasound image caused by intermixing different parts of the anatomical feature of interest is significantly reduced.

In an embodiment, the image processor arrangement is adapted to remove the shadow region from the one ultrasound image of the at least two ultrasound images by replacing said shadow region with a corresponding region of another ultrasound image from the at least two ultrasound images, said corresponding region not being shadowed by the invasive medical device. This works particularly well where the cardiac cycle is stable, i.e. highly repetitive with negligible variation in the cycle length, such that large acoustically shaded areas can be reliable replaced.

In a further embodiment, the image processor arrangement is adapted to remove the shadow region on the anatomical feature of interest caused by the invasive medical device from one of the ultrasound images of the at least two ultrasound images using a temporal grey level morphological closing algorithm. This technique may be used in scenarios where the cardiac cycle is unstable, but has the drawback that the size of the acoustically shaded region that can be filled in with such an algorithm is more limited.

Preferably, the image processing arrangement is further adapted to combine the augmented ultrasound images from the respective groups into a sequence of augmented ultrasound images imaging a full cardiac cycle such that a sequence of augmented ultrasound images in which the shadow regions have been removed from the anatomical feature of interest is available for evaluation or guidance to the medical practitioner operating the invasive medical device for instance.

In yet another embodiment, the image processing arrangement is further adapted to determine a position of an ultrasound probe with which the plurality of ultrasound images have been captured relative to the anatomical feature of interest; determine a position of the invasive medical device relative to the anatomical feature of interest; extrapolate an expected location of said shadow region on the anatomical feature of interest from the determined positions of the ultrasound probe and the invasive medical device; and remove the shadow region on the anatomical feature of interest in the extrapolated expected location based on the determined displacement of the invasive medical device. This further increases the accuracy of the shadow removal from the anatomical feature of interest because only those regions on the anatomical feature of interest for which it has been calculated that the invasive medical device blocks the ultrasound waves from the ultrasound probe from reaching those regions, thereby avoiding the correction of other parts of the image of the anatomical feature of interest, e.g. the correction of other regions erroneously considered artefacts.

The ultrasound image processing apparatus may be adapted to store the augmented ultrasound images from the respective groups in a data storage device such that the augmented ultrasound images may be evaluated at any suitable point in time, e.g. at a later date. Alternatively or additionally, the ultrasound image processing apparatus may be adapted to display the augmented ultrasound images from the respective groups on a display device, thereby facilitating real time evaluation of the augmented ultrasound images in which the shadow regions have been removed from the anatomical feature of interest in accordance with embodiments of the present invention.

According to another aspect, there is provided an ultrasound imaging system comprising the ultrasound image processing apparatus of any of the herein described embodiments and an ultrasound probe that can be communicatively coupled to the ultrasound image processing apparatus and is adapted to provide the ultrasound image processing apparatus with the plurality of ultrasound images. Such an ultrasound imaging system benefits from being able to provide its user with improved quality ultrasound images during procedures in which the progress of an invasive medical instrument such as a catheter, guide wire, needle and so on relative to other anatomical feature of interest is being imaged using the ultrasound imaging system.

According to yet another aspect, there is provided a method of processing a plurality of ultrasound images each ultrasound image imaging an invasive medical device relative to an anatomical feature of interest during a particular phase of a cardiac cycle, said anatomical feature of interest having a different shape at different phases of the cardiac cycle, the plurality of ultrasound images covering at least two cardiac cycles during which the invasive medical device is displaced relative to the anatomical feature of interest, the method comprising, with an image processor arrangement of an ultrasound image processing apparatus, receiving said plurality of ultrasound images; compiling a plurality of groups of the ultrasound images, wherein the ultrasound images in each group belong to the same phase of said cardiac cycles; and for each group: determining the displacement of the invasive medical device relative to the anatomical feature of interest between at least two ultrasound images in said group; and generating an augmented ultrasound image from one of the ultrasound images of the at least two ultrasound images by removing a shadow region on the anatomical feature of interest caused by the invasive medical device from said ultrasound image based on the determined displacement of the invasive medical device.

Consequently, with such a method the image processor arrangement of an ultrasound image processing apparatus may be configured to accurately remove shadow regions from an anatomical feature of interest that changes shape during different phases of the cardiac cycle such as a beating heart or another part of the cardiovascular system that changes shape during the cardiac cycle, as explained in more detail above.

In an embodiment, removing said shadow region comprises replacing the shadow region from the one ultrasound image of the at least two ultrasound images by replacing said shadow region with a corresponding region of another ultrasound image from the at least two ultrasound images, said corresponding region not being shadowed by the invasive medical device.

In another embodiment, removing said shadow region comprises removing the shadow region on the anatomical feature of interest caused by the invasive medical device from one of the ultrasound images of the at least two ultrasound images using a temporal grey level morphological closing algorithm.

The method may further comprise combining the augmented ultrasound images from the respective groups into a sequence of augmented ultrasound images imaging a full cardiac cycle such that a full cardiac cycle can be imaged in which each ultrasound image depicting a particular phase of the cardiac cycle has an improved resolution due to the accurate removal of the shadow region caused by the invasive medical device on the anatomical feature of interest.

In a particularly advantageous embodiment, the method further comprises determining a position of an ultrasound probe with which the plurality of ultrasound images have been captured relative to the anatomical feature of interest; determining a position of the invasive medical device relative to the anatomical feature of interest; extrapolating an expected location of said shadow region on the anatomical feature of interest from the determined positions of the ultrasound probe and the invasive medical device; and removing the shadow region on the anatomical feature of interest in the extrapolated expected location based on the determined displacement of the invasive medical device. Consequently, only regions on the anatomical feature of interest in which the shadow region can be present are considered for shadow removal, thereby avoiding erroneous correction of other imaged regions of the anatomical feature of interest.

The method may further comprise storing the augmented ultrasound images from the respective groups in a data storage device and/or displaying the augmented ultrasound images from the respective groups on a display device such that the augmented ultrasound images are available for evaluation at any suitable point in time, e.g. in real time or a later point in time.

According to yet another aspect, there is provided a computer program product comprising a computer readable storage medium having computer readable program instructions embodied therewith for, when executed on the image processor arrangement of the ultrasound image processing apparatus of any of the herein described embodiments, cause the image processor arrangement to implement the method of any of the herein described embodiments. Such a computer program product for example may be used to reconfigure, e.g. upgrade, existing ultrasound image processing apparatuses.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
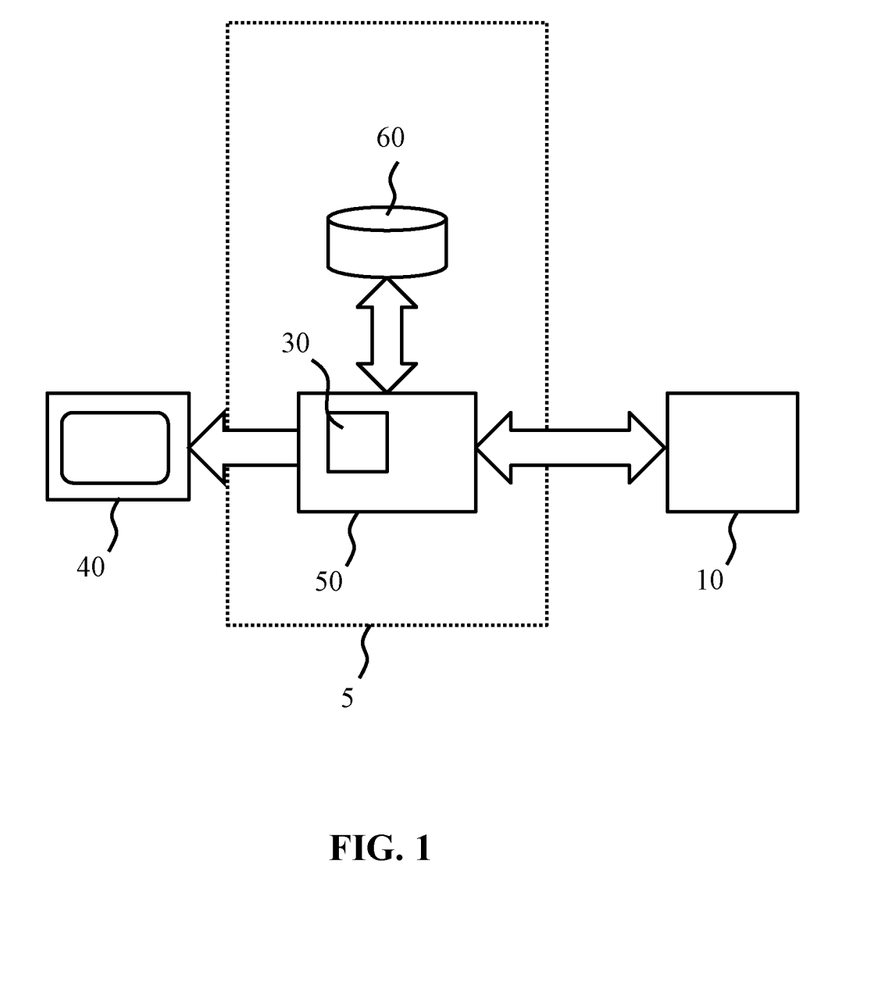
FIG. 1 schematically depicts an ultrasound image processing apparatus according to an embodiment.

FIG. 1 schematically depicts an ultrasound image processing apparatus 5 according to an example embodiment of the present invention. The ultrasound image processing apparatus 5 comprises an ultrasound image processor arrangement 50 at least including an image processor 30 although the ultrasound image processor arrangement 50 may comprise further processors as will be explained in more detail below by way of non-limiting example. The ultrasound image processor arrangement 50 may be communicatively coupled to a data storage arrangement 60, here shown as forming part of the ultrasound image processing apparatus 5 by way of non-limiting example only. It is for instance equally feasible that the data storage arrangement 60 is a remote data storage arrangement, e.g. a cloud-based data storage arrangement 60, which may be accessed by the ultrasound image processor arrangement 50 over a wired or wireless network, e.g. the Internet, a local area network, a mobile communications network, a point-to-point connection and so on, in which case the ultrasound image processing apparatus 5 further comprises a network interface (not shown), e.g. a wired network interface such as an Ethernet port or a wireless network interface such as a Bluetooth or Wi-Fi transceiver communicatively coupled to the ultrasound image processor arrangement 50 through which the ultrasound image processor arrangement 50 may communicate with the data storage arrangement 60. The data storage arrangement 60 may take any suitable shape, e.g. one or more memory devices, one or more magnetic storage disks, one or more solid state storage disks, one or more optical storage disks, and so on, or any combination thereof.

The ultrasound image processing apparatus 5 may further comprise a display 40, or at least be adapted to provide a communicative coupling between the ultrasound image processor arrangement 50 and the display 40 such that an ultrasound image processing result generated with the ultrasound image processor arrangement 50 may be displayed on the display 40 under control of the ultrasound image processor arrangement 50.

Figure 2:
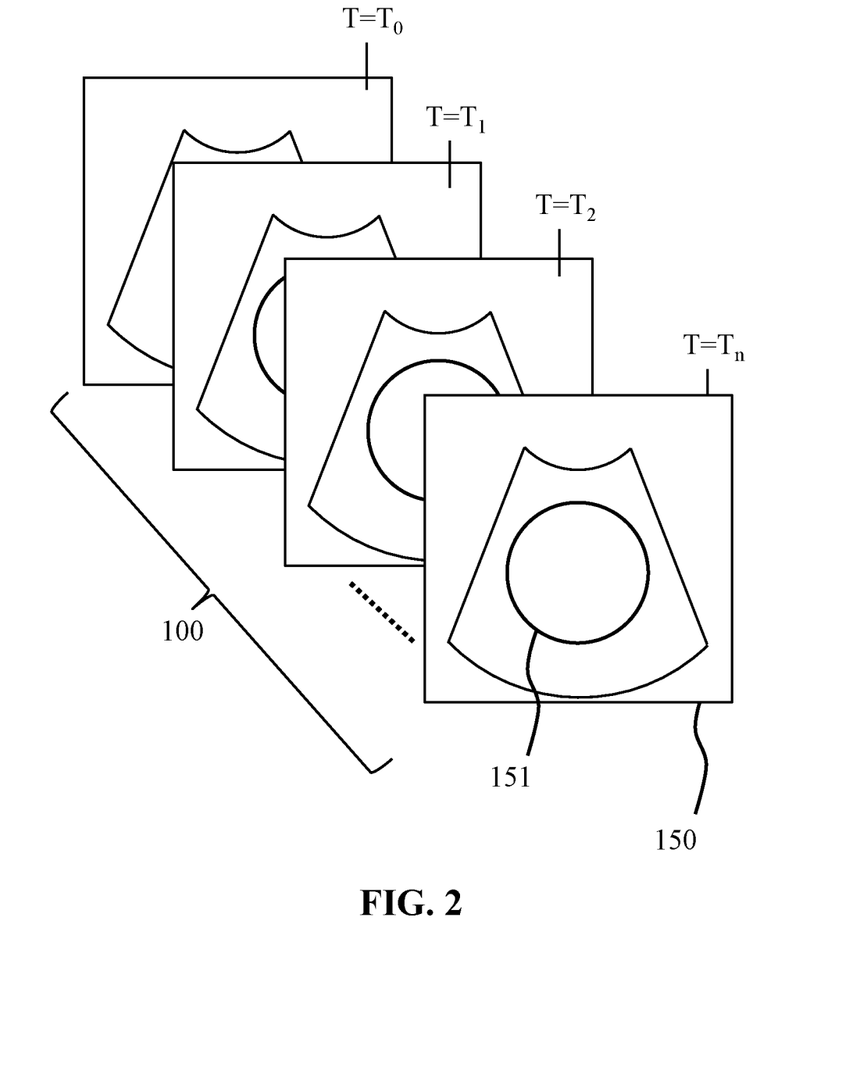
FIG. 2 schematically depicts a temporal sequence of ultrasound images for processing by such an ultrasound image processing apparatus.

The ultrasound image processing apparatus 5 is further adapted to provide a communicative coupling between the ultrasound image processor arrangement 50 and an ultrasound transducer 10, which typically is an ultrasound transducer for generating volumetric or 3-D ultrasound images. Such an ultrasound transducer 10 is well-known per se and is therefore not explained in further detail for the sake of brevity only. The ultrasound image processor arrangement 50 may receive a temporal sequence 100 of ultrasound images 150 as schematically depicted in FIG. 2. In the context of the present application, a temporal sequence 100 of ultrasound images 150 refers to a sequence of ultrasound images in which the same anatomical feature of interest 151 is imaged over a period of time (as depicted in FIG. 2 by the different time labels $T=T_0, T=T_1, T=T_2, T=T_n$), such that the sequence 100 comprises a plurality of ultrasound images 150 in which changes over time in the anatomical feature of interest can be visualized. This for example is particularly useful where the temporal sequence 100 of ultrasound images 150 images an anatomical feature of interest 151 undergoing shape changes during the cardiac cycle, e.g. having different shapes at different points or phases of the cardiac cycle, in which case each ultrasound image 150 captures the anatomical feature of interest 151 during a particular phase of the cardiac cycle. The anatomical feature of interest 151 may be the patient's beating heart or any other anatomical feature of interest 151, e.g. any other part of the cardiovascular system, undergoing shape changes during the cardiac cycle.

Each temporal sequence 100 typically constitutes a set of ultrasound images 150 imaging the anatomical feature of interest 151 over a full cardiac cycle, with different temporal sequences 100 imaging the anatomical feature of interest 151 during different cardiac cycles. The ultrasound image processor arrangement 50 typically receives a plurality of such temporal sequences 10 of ultrasound images 150 of the anatomical feature of interest 151. The ultrasound image processor arrangement 50 may receive the temporal sequences 100 of ultrasound images 150 directly from the ultrasound transducer 10 or alternatively may receive the temporal sequences 100 of ultrasound images 150 from the data storage arrangement 60 into which the temporal sequences 100 of ultrasound images 150 were previously stored, e.g. by the ultrasound image processing apparatus 5 for processing at a later date. The temporal sequences 100 of ultrasound images 150 may consist of a sequence of 2-D ultrasound image frames, which may be acquired with a 2-D ultrasound transducer 10 although preferably the temporal sequences 100 of ultrasound images 150 comprise a sequence of volumetric ultrasound images 150.

Figure 3:
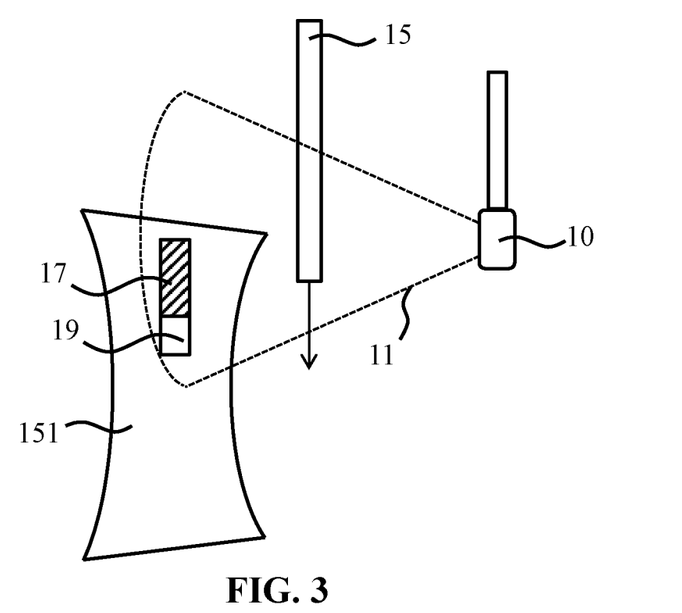
FIG. 3 schematically depicts an imaging arrangement during a first phase of a cardiac cycle.
Figure 4:
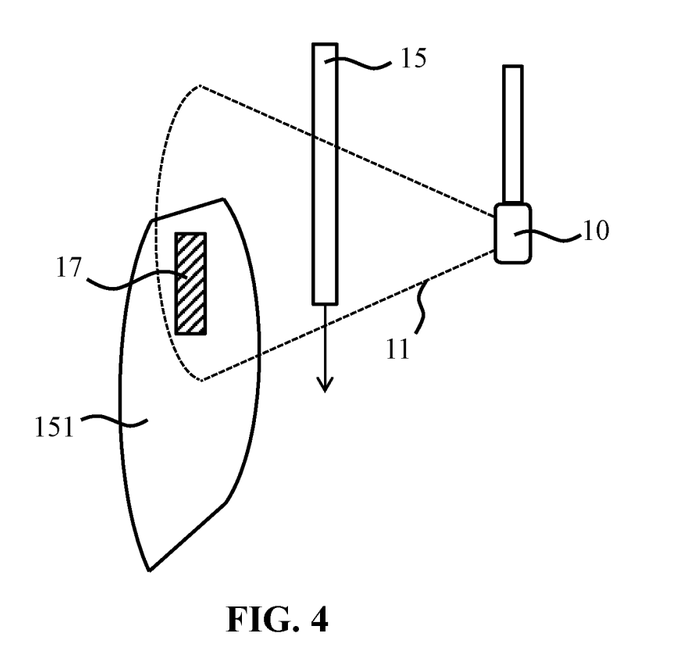
FIG. 4 schematically depicts an imaging arrangement during another phase of a cardiac cycle.

FIG. 3 and FIG. 4 schematically depict the imaging of an anatomical feature of interest 151 during different phases of the cardiac cycle with an ultrasound probe 10. The ultrasound probe 10 is typically positioned on a part of the body of the patient, such as the patient's chest in case of the imaging of the patient's heart. Importantly, during the medical procedure, the ultrasound probe 10 typically remains in the same position on the patient's body such that the ultrasound probe 10 can be considered a stationary source of ultrasound radiation. To this end, the ultrasound probe 10 may be secured in a probe holder or the like to ensure that the ultrasound probe 10 does not move (other than to follow body movements of the patient) during the medical procedure in which the invasive medical device 15 is inserted into the patient's body, e.g. through an artery or vein of the patient's cardiovascular system.

In FIG. 3, which depicts the anatomical feature of interest 151 as imaged by the ultrasound probe 10 during a first phase of a particular cardiac cycle, the anatomical feature of interest 151 has a first shape, whereas in FIG. 4, which depicts the anatomical feature of interest 151 as imaged by the ultrasound probe 10 during a different phase of the same particular cardiac cycle, the shape of the anatomical feature of interest 151 has changed it shape as a result of the cardiac cycle having entered a different phase. In FIG. 3, the invasive medical device 15 blocks a first part of the ultrasound beam 11 generated by the ultrasound probe 10, thereby casting an acoustic shadow 17 on the anatomical feature of interest 151, which is bordered by a non-shadowed region 19 in the direction of travel of the invasive medical device 15. In FIG. 4, this non-shadowed region 19 has been added to the acoustic shadow region 17 on the anatomical feature of interest 151, i.e. the acoustic shadow region 17 has increased in size due to the progression of the invasive medical device 15 into the ultrasound beam 11 generated with the ultrasound probe 10.

A commonly used technique to remove artefacts from images of a moving object captured at different points in time is temporal grey level morphological closing, in which the difference between the images at different points in time is attributed to the moving object, such that missing information in a first image of such a sequence of images can be filled in using information of a corresponding region of a further image of such a sequence in which the information is present, typically because in the further image this information is not obscured by the moving object. However, it will be understood that the difference between the respective ultrasound images 150 captured by the ultrasound probe 10 during the different phases of this cardiac cycle potentially are caused by two moving objects, namely the anatomical feature of interest 151 and the invasive medical device 15 being inserted (or removed) by the medical practitioner into the cardiovascular system of the patient.

Therefore, when artefact repair algorithms such as a temporal grey level morphological closing algorithm are applied to different ultrasound images 150 from within the same cardiac cycle, i.e. from the same temporal sequence 100, there is no guarantee that the invasive medical device 15 moves more between successive ultrasound images 150, e.g. volumetric images, than the anatomical feature of interest 151. Consequently, such artefact repair algorithms tend to mix data from different parts of the anatomical feature of interest 151 rather than from the same part of the anatomical feature of interest 151, thereby causing rather than removing artefacts in the augmented ultrasound image.

Figure 5:
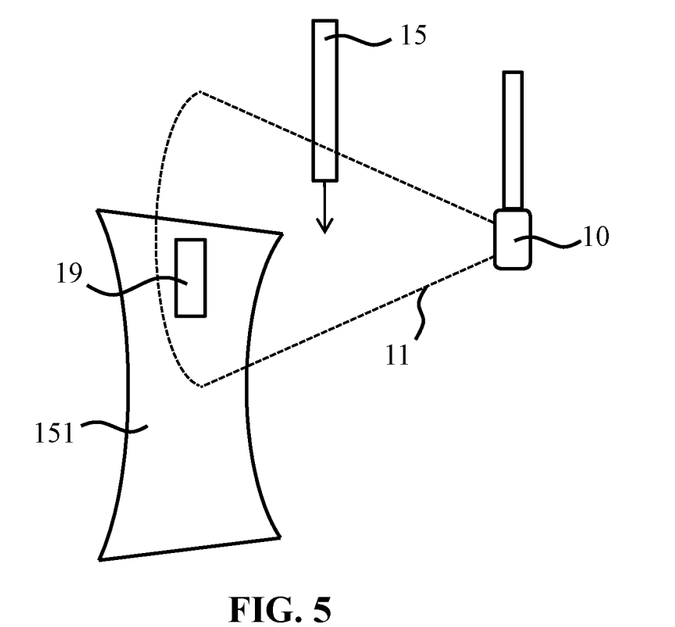
FIG. 5 schematically depicts an imaging arrangement during the first phase of a different cardiac cycle.
Figure 7:
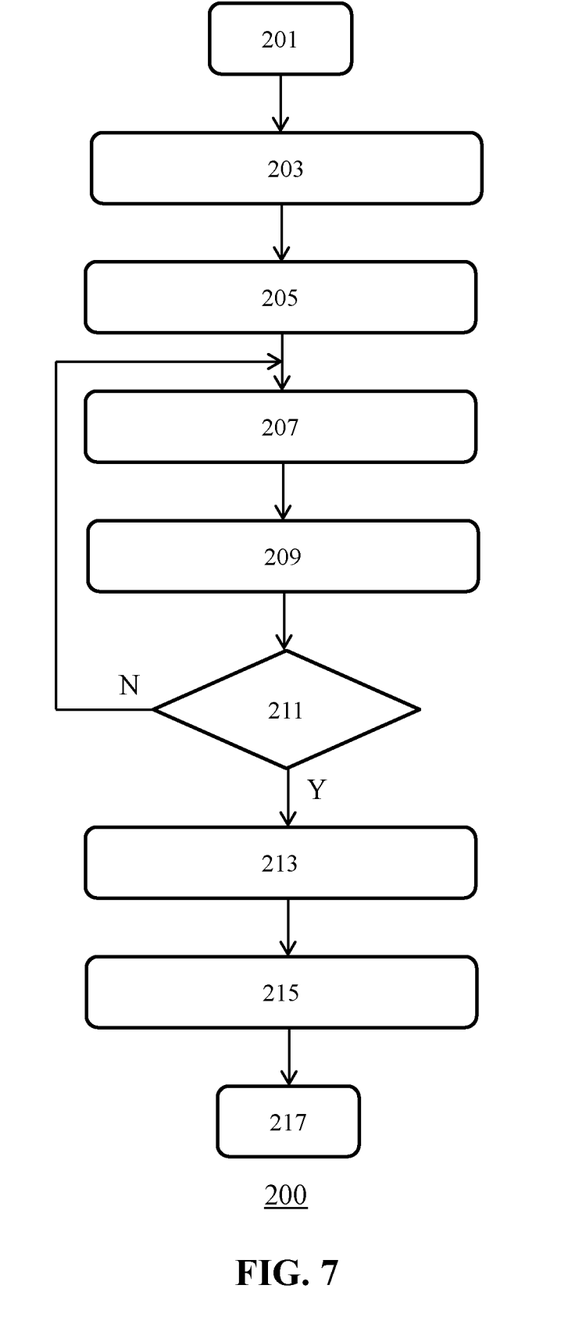
FIG. 7 depicts a flowchart of a method according to an embodiment.

However, the anatomical feature of interest 151 has a substantially constant shape at the same point in time, i.e. phase, of different cardiac cycles. This is schematically depicted in FIG. 5, which depicts the anatomical feature of interest 151 as imaged by the ultrasound probe 10 during a first phase of a later cardiac cycle compared to the particular cardiac cycle referred to in the detailed description of FIG. 3 and FIG. 4. As can be seen when comparing FIG. 3 and FIG. 5, the shape of the anatomical feature of interest 151 during the same phase of different cardiac cycles is at least approximately the same, such that the difference between ultrasound images 150 imaging the anatomical feature of interest 151 at the same phase of different cardiac cycles can be solely attributed to the movement of the invasive medical device 15. This insight is leveraged in embodiments of the present invention in which the image processor arrangement 50 of the ultrasound image processing apparatus 5 is configured to implement the method 200, a flow chart of which is shown in FIG. 7. The method 200 starts in 201, e.g. by switching on the ultrasound image processing apparatus 5, after which the method 200 proceeds to 203 in which the ultrasound image processor arrangement 50 receives a plurality of temporal sequences 100 of ultrasound images 150, which as previously mentioned preferably are 3-D or volumetric ultrasound images, with each temporal sequence 100 corresponding to a full cardiac cycle of the patient. The ultrasound image processor arrangement 50 may receive the plurality of temporal sequences 100 of the ultrasound images 150 from the ultrasound probe 10, e.g. in case of real-time processing of the ultrasound images 150 or may retrieve the plurality of temporal sequences 100 of the ultrasound images 150 from the data storage arrangement 60 instead.

In operation 205, the ultrasound image processor arrangement 50 generates groups or sequences of the ultrasound images 150, wherein for each group or sequence all ultrasound images 150 in that group or sequence were captured during the same phase of different cardiac cycles such that within each group or sequence the shape of the anatomical feature of interest 151 is at least approximately constant as explained above.

In operation 207, the ultrasound image processor arrangement 50 selects a group or sequence of the ultrasound images 150 and removes the shadow region 17 from the anatomical feature of interest 151 from one of the ultrasound images 150 of the selected group based on the displacement of the invasive medical device 15 across the ultrasound images 150 in the group. Typically, the shadow region 17 is removed at least from the most recent ultrasound image 150 within the group, i.e. from the ultrasound image 150 captured during the most recent cardiac cycle, although it is emphasized that it is not strictly necessary that the shadow region 17 is removed (only) from the most recent ultrasound image 150 in the group.

The removal of the acoustic shadow region 17 may be achieved using temporal closing algorithms such as a temporal grey level morphological closing algorithm in which the edge of the acoustic shadow region 17 in the ultrasound image 150 may be detected with an edge detection algorithm, such that the edge of the acoustic shadow region 17 can be identified in terms of coordinates within the ultrasound image 150 from which the acoustic shadow region 17 is to be removed. The ultrasound image processor arrangement 50 subsequently may evaluate the other ultrasound images 150 in the selected group in order to identify an ultrasound image 150 in the group for which at the identified coordinates no edge can be detected with the edge detection algorithm, which is indicative of this further ultrasound image 150 having a non-shadowed region 19 at the coordinates of the ultrasound image 150 from which the acoustic shadow region 17 is to be removed.

Figure 6:
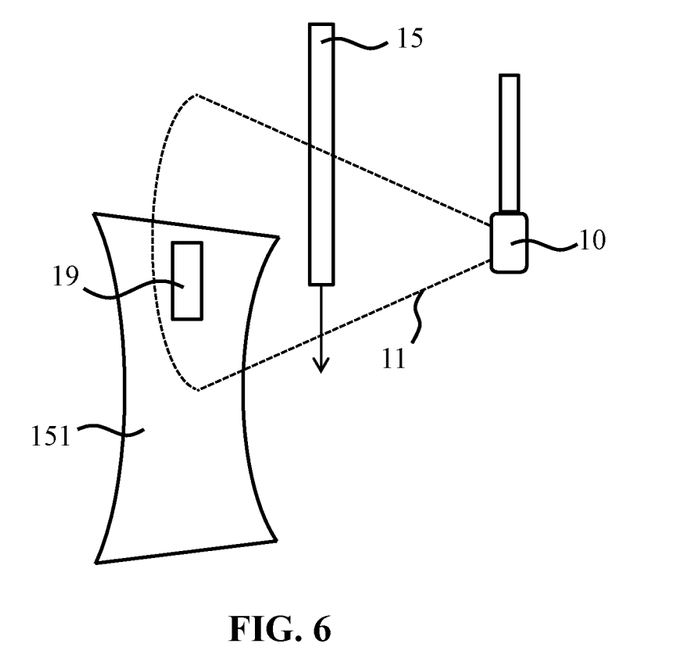
FIG. 6 schematically depicts an imaging arrangement including an augmented ultrasound image generated by the ultrasound image processing apparatus according to an embodiment.

The non-shadowed region 19 of this further ultrasound image 150 may be superimposed or otherwise inserted into the ultrasound image 150 from which the acoustic shadow region 17 is to be removed, thereby replacing the acoustic shadow region 17 with the non-shadowed region 19 from an earlier ultrasound image 150, thereby yielding an augmented ultrasound image 150 as schematically depicted in FIG. 6 in which the acoustic shadow region 17 of the anatomical feature of interest 151 has been replaced by a non-shadowed region 19 from the earlier ultrasound image 150, such that the region of the anatomical feature of interest 151 in the acoustic shadow of the invasive medical device 15 becomes visible in the augmented ultrasound image 150, thereby improving the resolution of this ultrasound image.

In a further refinement, the ultrasound image processor arrangement 50 is adapted to estimate the location of the shadow region 17 of the ultrasound image 150 based on the positioning of the ultrasound probe 10 relative to the anatomical feature of interest 151. To this end, the position of the ultrasound probe 10 relative to the anatomical feature of interest 151 may be registered by the ultrasound image processor arrangement 50 such that upon the appearance of the invasive medical device 15 in between the ultrasound probe 10 and part of the anatomical feature of interest 151, the expected location of the shadow region 17 on the anatomical feature of interest 151 is estimated by the ultrasound image processor arrangement 50 to lie in the common plane of the ultrasound probe 10 and the invasive medical device 15. This may further require the determination of the location of the invasive medical device 15 within the body of the patient, as will be understood by the skilled person. As such location determination techniques are well-known per se, they are not explained here in further detail for the sake of brevity only. In this manner, the edge detection algorithm implemented by the ultrasound image processor arrangement 50 may only consider edges in the vicinity of the estimated location of the shadow region 17 in the ultrasound image 150 to be augmented, thereby reducing the risk that the edge detection algorithm detect an edge of a region other than the shadow region 17 in the ultrasound image 150 to be augmented.

Upon removal of the acoustic shadow region 17 from the ultrasound image 150 to be augmented, the ultrasound image processor arrangement 50 checks in operation 211 if all groups of ultrasound images 150 corresponding to the different phases of the captured cardiac cycles have been processed. If this is not the case, the method 200 reverts back to operation 207 in which the ultrasound image processor arrangement 50 selects the next group or sequence of ultrasound images 150 to be processed, i.e. the group corresponding to the next phase of the cardiac cycle. Once all groups have been processed in this manner, the ultrasound image processor arrangement 50 may proceed to operation 213 in which the ultrasound image processor arrangement 50 generates a sequence of the augmented ultrasound images 150 by combining the augmented ultrasound images 150 from each group, thereby compiling a sequence of images typically imaging the anatomical feature of interest 151 during a full cardiac cycle for which the acoustic shadow regions 17 from the respective augmented ultrasound images have been removed as previously explained. It should be understood that operation 213 is optional, as alternatively the ultrasound image processor arrangement 50 may generate an output of each individual augmented ultrasound image 150 upon its generation.

In operation 215, the ultrasound image processor arrangement 50 generates an output of the (sequence of) augmented ultrasound images 150. This output for instance may be in the form of a dataset for storage in the data storage arrangement 60 or alternatively may be in the form of a dataset for display on the display 40. It is of course equally feasible that the ultrasound image processor arrangement 50 generates such outputs both for storage in the data storage arrangement 60 and for display on the display 40. Subsequently, the method 200 terminates in 217. It is noted for the avoidance of doubt that the method 200 as described above has been described by way of non-limiting example only and that several modifications to the method 200 may be contemplated without departing from the teachings of the present invention. For example, different acoustic shadow removing algorithms that are well-known per se to the skilled person may be deployed by the skilled person. As another example, the method 200 may be adapted such that rather than sequentially processing the plurality of groups of ultrasound images 150 to generate the augmented ultrasound images from which the shadow region 17 has been removed, at least some of these groups may be processed by the ultrasound image processor arrangement 50 in parallel in order to accelerate the image processing. Other such obvious modifications to the method 200 will be immediately apparent to the skilled person.

Figure 8:
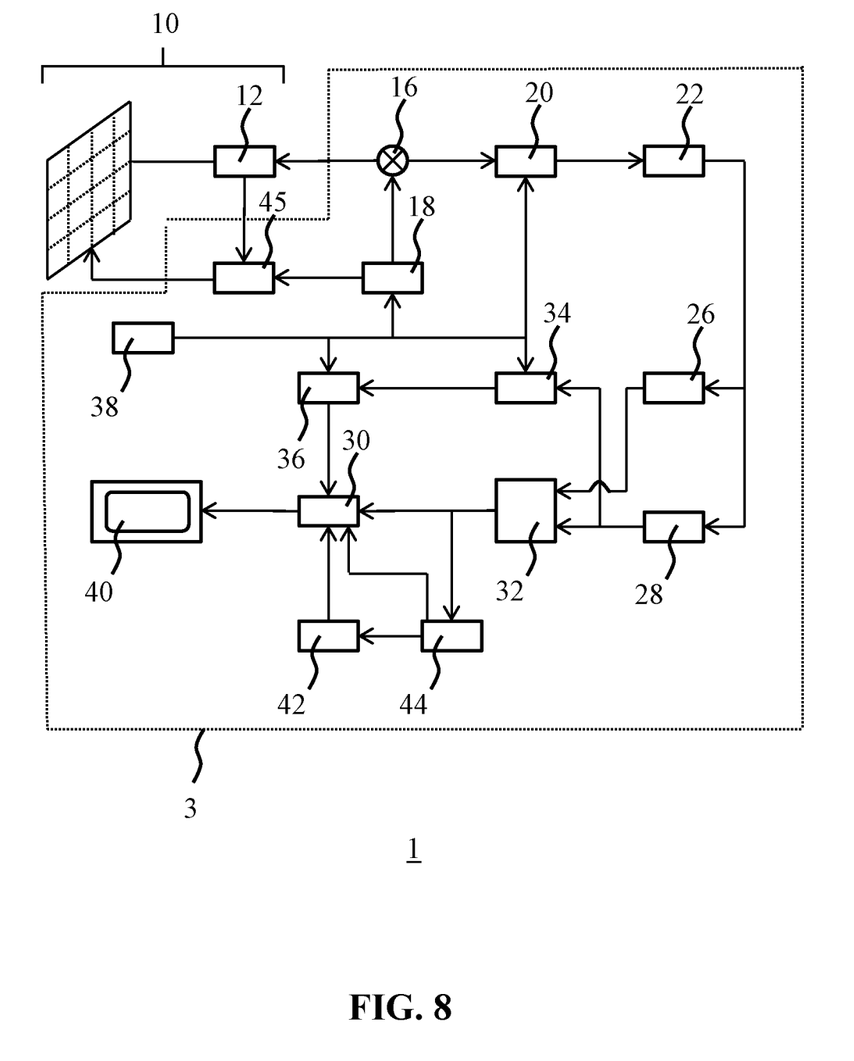
FIG. 8 schematically depicts an ultrasound imaging system according to an example embodiment.

FIG. 8 schematically depicts an example embodiment of an ultrasound imaging system 1 with an ultrasound probe or transducer 10, e.g. an array of ultrasound transducer element tiles (transducer elements) comprising multiple transducer elements, which may be arranged in a one-dimensional or two-dimensional array of transducer cells or elements. Any suitable type of ultrasound transducer elements may be used for this purpose, e.g. piezoelectric transducer (PZT) elements, capacitive micro-machined ultrasound transducer (CMUT) elements, piezoelectric micro-machined transducer (PMUT) elements, and so on, although CMUT elements are particularly preferred, in particular over (PZT) elements due to their superior (adjustable) resonance frequency range, which make CMUT elements particularly suitable for patient monitoring purposes. As such transducer elements are well-known per se, they will not be explained in further detail for the sake of brevity only. The array of transducer cells may be arranged as a phased array to facilitate beam steering of an ultrasound beam generated with the ultrasound transducer 10. Again, such beam steering is well-known per se and will not be explained in further detail for the sake of brevity only. Preferably, the ultrasound transducer 10 has a 2-D array of ultrasound transducer element tiles capable of generating 3-D or volumetric ultrasound images.

The ultrasound probe 10 typically is operable in a transmit mode in which ultrasound beams are generated and a receive mode in which the ultrasound probe 10 is operable to receive echo signals induced by the generated ultrasound beams within the body of the individual being imaged with the ultrasound probe 10. The ultrasound probe 10 typically is controlled by a terminal 3 including the ultrasound image processing apparatus 5.

The ultrasound probe 10 may be coupled to a microbeam former 12, which may be integrated in the ultrasound probe 10, which controls transmission and reception of signals by the ultrasound transducer cells (or clusters thereof) of the ultrasound probe 10. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to the terminal 3, e.g. a patient interface module or the like, comprising a transmit/receive (T/R) switch 16 which switches between transmission and reception modes and protects the main beam former 20 from high energy transmit signals when a microbeam former is not present or used and the ultrasound probe 10 is operated directly by the main system beam former 20. The transmission of ultrasonic beams from the ultrasound probe 10 under control of the microbeam former 12 may be directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the ultrasound probe 10, or at different angles for a wider field of view. The transducer controller 18 may be coupled to control the voltage source 45 for the ultrasound transducer array 10. For instance, the power supply 45 may set the DC and AC bias voltage(s) that are applied to CMUT cells in case of a CMUT probe 10, e.g. to operate the one or more CMUT cells of the CMUT elements in collapse mode, as is well-known per se.

The power supply 45 may optionally comprise separate stages for providing the DC and AC components respectively of the stimulus of the CMUT cells, e.g. in transmission mode. A first stage may be adapted to generate the static (DC) voltage component and a second stage may be adapted to generate an alternating variable voltage component having a set alternating frequency, which signal typically is the difference between the overall drive voltage, i.e. stimulus, and the aforementioned static component thereof. The static or bias component of the applied drive voltage preferably meets or exceeds the threshold voltage when forcing the CMUT elements into their collapsed states, i.e. when operating the CMUT elements in collapsed mode. This has the advantage that the first stage may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component.

Other suitable embodiments of the power supply 45 should be apparent, such as for instance an embodiment in which the power supply 45 contains three discrete stages including a first stage for generating the static DC component of the CMUT drive voltage, a second stage for generating the variable DC component of the drive voltage and a third stage for generating the frequency modulation component of the signal, e.g. a pulse circuit or the like. It is summarized that the power supply 45 may be implemented in any suitable manner. It is furthermore emphasized that the power supply 45 is not limited to the operation of CMUT elements; any type of transducer element may be controlled by a suitably adapted power supply 45, as is well-known per se.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells. In this way the signals received by thousands of transducer cells of a transducer array 10 can contribute efficiently to a single beam-formed signal.

The beam-formed signals are coupled to a signal processor 22, which may form part of the image processor arrangement 50 of the image processing apparatus 5, which in the present embodiment is integrated in the terminal 3 by way of non-limiting example only. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28, which processors also may form part of the image processor arrangement 50. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44, both which may also form part of the image processor arrangement 50. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42, which also may form part of the image processor arrangement 50, converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 forming part of the image processor arrangement 50 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface may also be coupled to the transmit controller 18 to control the generation of ultrasound signals from the ultrasound probe 10 and hence the images produced by the transducer array and the ultrasound system. The user interface may also be coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasound imaging system 1 is intended to give a non-limiting example of such an ultrasonic diagnostic imaging system. The skilled person will immediately realize that several variations in the architecture of the ultrasound imaging system 1 are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person. The ultrasound imaging system 1 may be used in a variety of interventional procedures such as transesophageal echocardiography (TEE), Inter-Cardiac Echography (ICE), Trans-Thoracic Echography (TTE) and so on.

The above described embodiments of the method 200 executed by the image processor arrangement 50 may be realized by computer readable program instructions embodied on a computer readable storage medium having, when executed on an image processor arrangement 50 of an ultrasound image processing apparatus 5, e.g. a standalone ultrasound image processing apparatus 5 or an ultrasound image processing apparatus 5 integrated in a user terminal 3, cause the image processor arrangement 50 to implement the method 200. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the ultrasound image processing apparatus 5 is adapted to retrieve the computer readable program instructions from such a computer readable storage medium and to create a new computer readable storage medium by storing the retrieved computer readable program instructions in a data storage arrangement 60, e.g. in a memory device or the like forming part of the data storage arrangement.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound image processing apparatus comprising an image processor arrangement adapted to:
   receive a plurality of ultrasound images obtained by an ultrasound probe, each ultrasound image imaging an invasive medical device relative to an anatomical feature of interest within a patient body during a particular phase of a cardiac cycle, said anatomical feature of interest having a shape that is different at different phases of the cardiac cycle, the plurality of ultrasound images covering at least two cardiac cycles during which the invasive medical device is displaced relative to the anatomical feature of interest and the ultrasound probe;
   compile a plurality of groups of the ultrasound images, wherein the ultrasound images in each group belong to a same phase of said at least two cardiac cycles; and
   for each group:
      determine the displacement of the invasive medical device relative to the anatomical feature of interest between a first ultrasound image and a second ultrasound image in said group, wherein a change between the first ultrasound image and the second ultrasound image is attributable to the displacement of the invasive medical device;
      identify a first set of coordinates representative of an edge of an acoustic shadow region occurring within the first ultrasound image as a result of the displacement;
      identify a corresponding second set of coordinates within the second ultrasound image;
      determine whether the edge of the acoustic shadow region is present within the second ultrasound image at the second set of coordinates;
      in response to determining that the edge of the acoustic shadow region is not present at the second set of coordinates, overlay one or more pixels occurring at the second set of coordinates from the second ultrasound image on the first ultrasound image at the first set of coordinates, thereby generating an augmented ultrasound image; and
      output the augmented ultrasound image to a display.

2. The ultrasound image processing apparatus of claim 1, wherein the overlay of the one or more pixels by the image processor arrangement comprises a removal of the acoustic shadow region from the first ultrasound image.

3. The ultrasound image processing apparatus of claim 1, wherein the image processor arrangement is further adapted to combine the augmented ultrasound images from the respective plurality of groups into a sequence of augmented ultrasound images imaging a full cardiac cycle.

4. The ultrasound image processing apparatus of claim 1, wherein the image processor arrangement is further adapted to:
   determine a position of the ultrasound probe relative to the anatomical feature of interest;
   determine a position of the invasive medical device relative to the anatomical feature of interest;
   extrapolate an expected location of said acoustic shadow region from the determined positions of the ultrasound probe and the invasive medical device; and
   remove the acoustic shadow region in the extrapolated expected location based on the determined displacement of the invasive medical device.

5. The ultrasound image processing apparatus of claim 1, wherein the image processor arrangement is further adapted to store the augmented ultrasound images from the respective plurality of groups in a data storage device.

6. The ultrasound image processing apparatus of claim 5, wherein the image processor arrangement is further adapted to output a sequence of augmented ultrasound images to the display.

7. The ultrasound image processing apparatus of claim 1, wherein the image processor arrangement is further adapted to estimate a location of the acoustic shadow region of the first ultrasound image based on a position of the ultrasound probe relative to the anatomical feature of interest.

8. An ultrasound imaging system comprising:
   the ultrasound image processing apparatus of claim 1; and
   the ultrasound probe, wherein the ultrasound probe is adapted to be communicatively coupled to the ultrasound image processing apparatus and is adapted to provide the ultrasound image processing apparatus with the plurality of ultrasound images.

9. A method of processing a plurality of ultrasound images obtained by an ultrasound probe, each ultrasound image imaging an invasive medical device relative to an anatomical feature of interest within a patient body during a particular phase of a cardiac cycle, said anatomical feature of interest having a shape that is different at different phases of the cardiac cycle, the plurality of ultrasound images covering at least two cardiac cycles during which the invasive medical device is displaced relative to the anatomical feature of interest and the ultrasound probe, the method comprising, with an image processor arrangement of an ultrasound image processing apparatus:
   receiving said plurality of ultrasound images;
   compiling a plurality of groups of the ultrasound images, wherein the ultrasound images in each group belong to a same phase of said at least two cardiac cycles; and
   for each group:
      determining the displacement of the invasive medical device relative to the anatomical feature of interest between a first ultrasound image and a second ultrasound image in said group, wherein a change between the first ultrasound image and the second ultrasound image is attributable to the displacement of the invasive medical device;
      identifying a first set of coordinates representative of an edge of an acoustic shadow region occurring within the first ultrasound image as a result of the displacement;
      identifying a corresponding second set of coordinates within the second ultrasound image;
      determining whether the edge of the acoustic shadow region is present within the second ultrasound image at the second set of coordinates;
      in response to determining that the edge of the acoustic shadow region is not present at the second set of coordinates, overlaying one or more pixels occurring at the second set of coordinates from the second ultrasound image on the first ultrasound image at the first set of coordinates, thereby generating an augmented ultrasound image; and
      outputting the augmented ultrasound image to a display.

10. The method of claim 9, wherein the overlaying the one or more pixels comprises a removal of the acoustic shadow region from the first ultrasound image.

11. The method of claim 9, further comprising combining the augmented ultrasound images from the respective plurality of groups into a sequence of augmented ultrasound images imaging a full cardiac cycle.

12. The method of claim 9, further comprising:
  determining a position of the ultrasound probe relative to the anatomical feature of interest;
  determining a position of the invasive medical device relative to the anatomical feature of interest;
  extrapolating an expected location of said acoustic shadow region from the determined positions of the ultrasound probe and the invasive medical device; and
  removing the acoustic shadow region in the extrapolated expected location based on the determined displacement of the invasive medical device.

13. The method of claim 9, further comprising storing the augmented ultrasound images from the respective plurality of groups in a data storage device and/or displaying the augmented ultrasound images from the respective plurality of groups on a display device.

14. The method of claim 9, further comprising estimating a location of the acoustic shadow region of the first ultrasound image based on a position of the ultrasound probe relative to the anatomical feature of interest.

* * * * *